United States Patent [19]

Farwell et al.

[11] 4,072,044
[45] Feb. 7, 1978

[54] LIQUID LEVEL CONTROLLER AND SOIL TEST INSTRUMENT

[76] Inventors: Allen C. Farwell; Dale E. Farwell; Duane C. Farwell, all of Rte. 1, Cottage Grove, Wis. 53527

[21] Appl. No.: 664,190

[22] Filed: Mar. 5, 1976

[51] Int. Cl.² .................. G01F 23/10; G01N 15/08
[52] U.S. Cl. .......................................... 73/38; 73/291
[58] Field of Search ............... 73/38, 73, 155, 291, 73/304 R; 137/386, 391, 393

[56] References Cited

U.S. PATENT DOCUMENTS

| 2,540,096 | 2/1951 | Bull | 73/38 |
|---|---|---|---|
| 3,548,635 | 12/1970 | Hutchinson et al. | 73/38 |
| 3,892,126 | 7/1975 | Curtin | 73/38 |
| 3,945,247 | 3/1976 | Anderson | 73/73 |

Primary Examiner—Richard C. Queisser
Assistant Examiner—Joseph W. Roskos
Attorney, Agent, or Firm—Keith Schoff

[57] ABSTRACT

A portable, automatic liquid level monitoring and recording instrument is disclosed for use in measuring the capacity of soils to absorb water. A self-contained power source, timer and vertically biasable recording probe are housed as a cylindrical package disposed for placement in a shallow bore hold and connected to a reserve water supply. The probe, carrying an ink filled stylus, scribes a graph lining the inside of the cylinder during excursions initiated by timer actuation, the direction of probe traverse being reversed by completion of a circuit when the probe contacts water. Water is replenished to the borehole to datum level automatically after completion of the downward traverse of the probe.

6 Claims, 3 Drawing Figures

LIQUID LEVEL CONTROLLER AND SOIL TEST INSTRUMENT

FIELD OF INVENTION

Liquid level controllers are widely used for maintaining the levels to which vessels are kept filled, one particular application being in connection with site evaluation and foundation engineering studies for land improvement and building projects wherein water is provided and maintained at a prescribed depth in a shallow bore hole with loss to seepage being a measure of the capacity of the soil to absorb water. Percolation testing, as the procedure is popularly known, is a requirement prescribed by building codes in many jurisdictions and involves periodic observation being made of the elevational drop in water level in a bore hole which is replenished with water to a prescribed depth after each observation, the procedure being continued until seepage diminishes sufficiently to indicate ground saturation. Observations are commonly logged at half-hourly intervals and may continue for one or more days before soil saturation occurs. Attendance of personnel at all hours of day and night has heretofore been required for making the necessary observations, and has imposed a costly burden which has entailed viewing and measuring the water level at sub-grade elevation.

SUMMARY OF THE INVENTION

A portable, battery powered, timer controlled, reversible motor driven liquid level controller is disclosed, suitable for use in general applications, and particularly discribed as a percolation testing and recording instrument. The described embodiment incorporates a movable, depth sensing, recording probe mounted for being vertically driven, by a screw lead threaded shaft of a reversible drive motor inserted in a water filled bore hole, to contact water in the hole and complete an electric circuit which reverses rotation of the motor, retrieves the probe and causes a water supply valve to open. Water is replenished to the bore hole until sensed at a prescribed elevation by means which closes the water valve. A stylus attached to the probe scribes a graph lining the inner surface of a cylindrical instrument wall and is forwardly indexed circumferentially of the instrument along the horizontal axis of the graph at the completion of each excursion of the probe to produce an area of solid vertical scribing which delineates a curve which approaches as an asymptote the prescribed water level fill elevation, a condition which if achieved would indicate no seepage and soil saturation. The described instrument automates the procedure for conducting soil percolation tests and eliminates the need for attendance of personnel except for setting the instrument in place at the commencement of test and retrieving it at the completion of test, and effects substantial labor savings and cost economy and achieves increased accuracy of readings.

DESCRIPTION OF THE INVENTION

Figure 1:
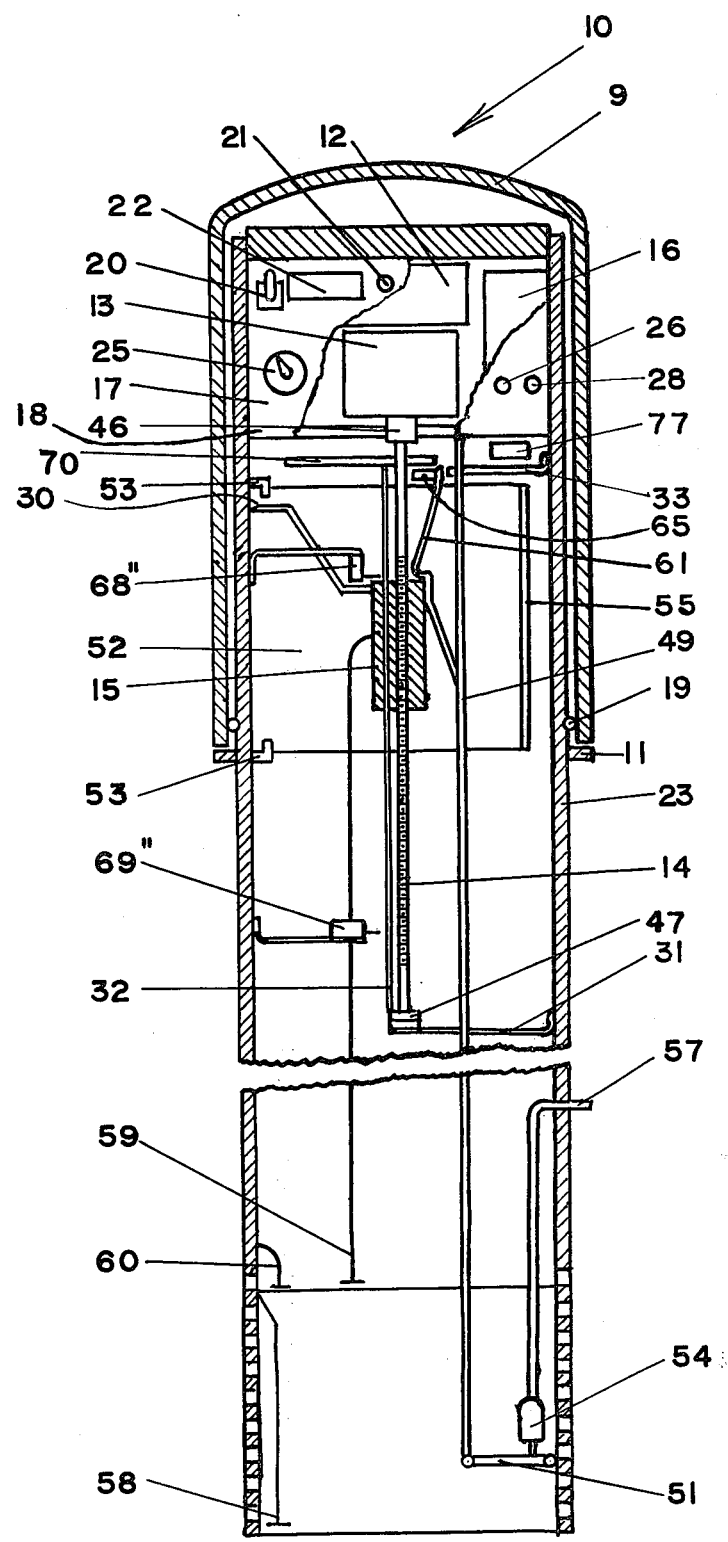
FIG. 1 is a cross-sectional elevation of an embodiment of the invention.
Figure 2:
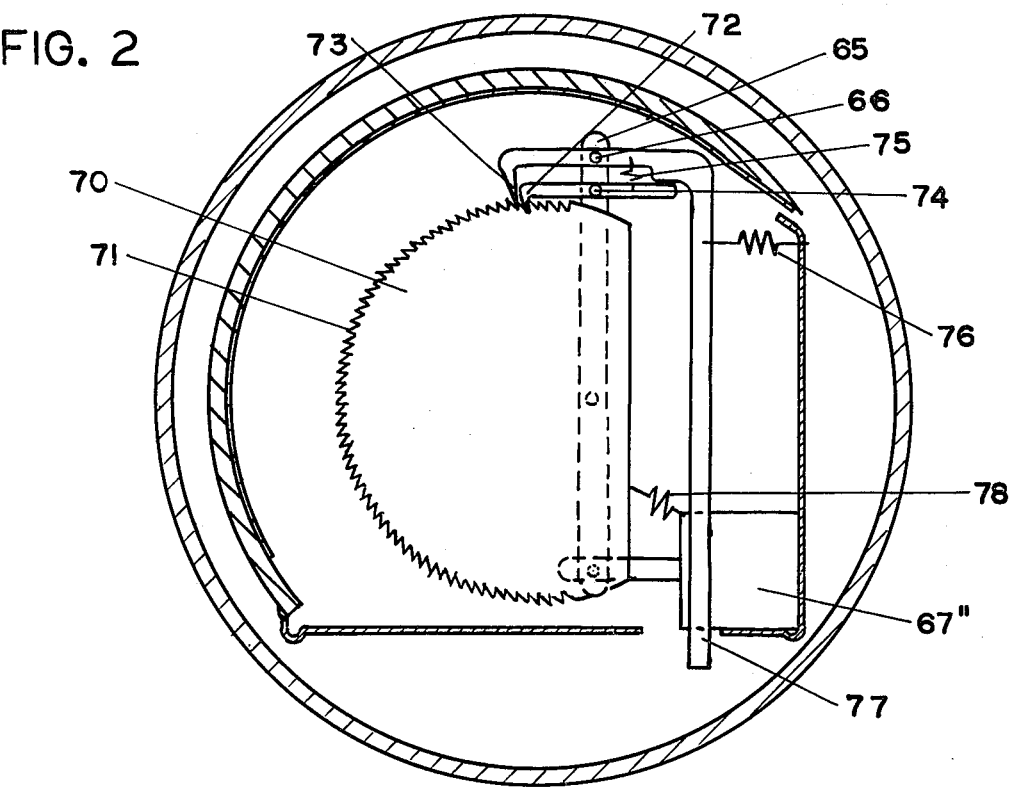
FIG. 2 is a cross-sectional plan view from section line 2—2 of FIG. 1.
Figure 3:
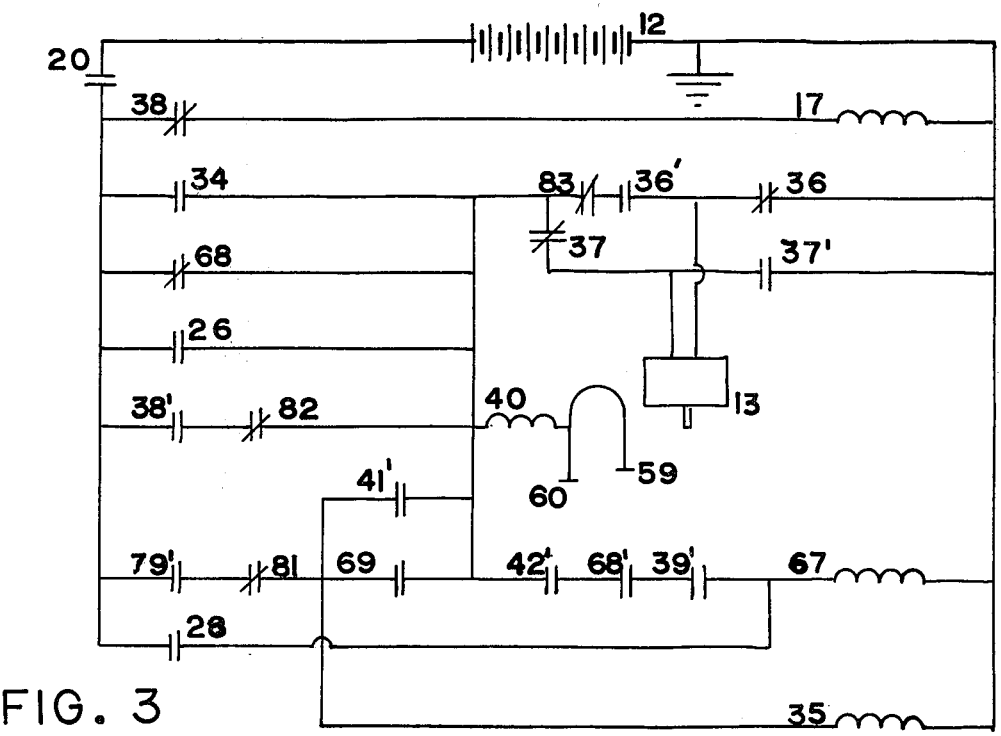
FIG. 3 is a schematic wiring diagram of the embodiment of FIG. 1.

in FIGS. 1 and 2 liquid level controlling, monitoring and recording instrument 10 is shown cylindrically configured for placement in bore holes in field locations to measure in situ the capacity of undisturbed soils to absorb water. Instrument 10 may be of any convenient size or configuration as desired for use as a liquid level controller, but for use as a percolation tester, as shown, the instrument is preferably about 3 feet in length and 4 inches in diameter. Rim 11 provides a seat for cover 9 witn O-ring 19 being provided as a gasket to prevent dirt and moisture from entering into the cover enclosure. Rechargable 12 volt battery 12 as shown is preferred as a power source for instrument 10, but any other suitable power source may be provided such as dry cell batteries, transformer and rectifier for connection to alternating current distribution lines, or if suitable instrument components are provided, alternating current may be used directly. Reversibly operable motor 13 is mounted with output shaft 14 extending downward centrally of instrument 10 with shaft 14 externally threaded for operably traversing internally threaded follower 15 mounted thereon. Relay box 16 disposed adjacent motor 13 houses relays and circuitry shown schmatically in FIG. 3 and operationally described below. Clock timed switch 17 preferably comprises low current consuming means such as a capacitor discharge, impulse drive stepping switch, such components being well known for use in electrical servo mechanisms.

Transverse bulkhead 18 divides instrument 10 to provide an isolated compartment housing the described power source, relays, motor and clock timed switch components for protecting the components from exposure to dirt and moisture. Motor shaft 14 runs in upper and lower bearings 46 and 47 which are mounted, respectively, in bulkhead 18 and bracket 31. Graph paper 52 is printed with rectilinear coordinates and is aligned by guideways 53, extending through access slot 55 with a piece of pressure sensitive tape (not shown) attached to the free end serving to fix it in place.

Internally threaded follower 15 mounted on motor shaft 14 carries scribing stylus 30 resiliently biased to press firmly against graph paper 52, the latter being of "carbonless carbon paper" variety if stylus 30 is a scribing stylus, or conventional graph paper is stylus 30 carries an ink filled pen. Follower 15 and stylus 30 are aligned radially of instrument 10 by rod guide 32 which depends from sector plate 70 to which it is fixed, and with which it incrementally rotates within instrument 10 as hereinafter described. Valve rod 49 depends within instrument 10 fixed radially in position by upper guide bracket 33 and lower guide bracket 31. The base of valve rod 49 pivotally connects to linkage 51 which is biasable in the manner of a lever to open water valve 54 when valve rod 49 is raised and to be removed from contact enabling valve 54 to be self-closing when valve rod 49 is lowered. Fill valve 54 is served by supply tube 57 which is connectable to a reservoir or pipe, not shown.

Instrument 10 is designed for being placed in a bore hole with about 7 inches of length being below grade, such length being perforated with screened openings to enable water to readily escape from the instrument into the surrounding soil and to prevent at least coarse sediment from entering the instrument.

Retaining clip 61 fixed to the upper portion of valve rod 49 comprises resilient latching means which is urged toward follower 15 to extend above the follower and be lifted thereby to raise valve rod 49 as follower approaches the upward limit of vertical traverse. Retaining clip 61 is physically displaced from its latched position bearing on the upper surface of follower 15 by operable actuation of ratchet arm 65 which contacts it and dislodges it, enabling valve rod 49 to drop unsupported about 1 inch thereby releasing linkage 51 actuation of water valve 54. Follower 15 in the same transverse motion which dislodges retaining clip 61 from support on follower 15 also contacts means opening contacts 81 and 82, interrupting the circuits to all instrument components except clock timed switch 17 which is energized through closed contact 38. With all circuits open except to the clock timed switch 17, minimal current is drained from power source 12 until another cycle of operation is commenced after a pre-determined time lapse. Actuation of ratchet arm 65 by solenoid operator 67″ responding to current in solenoid coil 35 moves the ratchet arm to the right as shown in FIG. 2 about pivot pin 66 causing ratchet advancing pawl 72 to similarly move rightward with ratchet arm 65 to which it is pivotally attached, incrementally rotating sector plate 70 to advance by one tooth 71 under ratchet holding pawl 73. When ratchet arm 65 returns to unactuated position after contacts 81 and 82 are opened as above described, sector plate 70 is retained in the position to which it was advanced and ratchet advancing pawl 72 rides over one tooth 71 against the urging of spring 75 to engage sector plate 70 in a new position. Sector plate 70 may be reset to unactuated position by manually moving handle 77 of ratchet holding pawl 73 to the left as shown in FIG. 2 against the urging of spring 76 to release both pawls 72 and 73 from engagement with teeth 71 of sector plate 70, enabling return spring 78 to rotate sector plate 70 courter clockwise to unactuated position as shown. Handle 77 is then released and the instrument is properly in condition for beginning a new test record.

Controls for instrument 10 are arrayed on the upper portion of the instrument under cover 9. Actuation of manual push button test switch 26 energizes motor 13 independent of contact terminal 34 of clock timed switch 17, providing for test cycling of instrument 10. Actuation of push button switch 28 energizes solenoid operator 67″ independent of contacts 81 and 82, providing means for advancing stylus 30, which rotates together with sector plate 70. Manual actuation of main power switch 20 energizes the circuits of instrument 10 with voltmeter 22 and voltmeter test switch 21 being provided across battery 12 to test the electrical charge on the battery. Selector dial 25 on clock timed switch 17 enable selection to be made for actuation of switch 17 from a scale of timed interval settings.

Upper limit switch 68″ and lower limit switch 69″ are provided for deenergizing motor 13 and reversing operation of motor 13, respectively, when the limit switches are contacted by follower 15. Lower limit switch 69″ will only be contacted by follower 15 in the event that water recedes to an elevation beyond the lowest reach of electrode 59 carried by follower 15. In the usual circumstance electrode 58 will be immersed in water at all times and provide a current return path to battery 12 for a circuit established by electrode 59 contacting water during descent of follower 15, causing motor 13 to reverse rotation before lower limit switch 69″ is contacted. Follower 15 carrying electrode 59 then ascends within instrument 10 lifting electrode 59 from contact with water and contacts retaining clip 61 to raise valve rod 49 and open water valve 54 before tripping upper limit switch 68″ to close contact 68′ and open contacts 68 and 83 which stops motor 13. Water rises in instrument 10 from open valve 54 until fixed electrode 60 is wetted to again complete a circuit through electrode 58 which energizes solenoid operator 67″, biasing ratchet arm 65 to dislodge retaining clip 61 dropping valve rod 49 and closing water valve 54, and also opening contacts 81 and 82 switching all circuits except that of clock timed switch 17, to open position. The operational sequence more particularly described with relation to FIG. 3 requires main power switch 20 to be manually closed to actuate clock timed switch 17 which controls contact 34, closing it after a pre-determined time interval and causing it to remain closed for a finite time interval of sufficient length to enable motor 13 to begin rotation of shaft 14 and traverse follower 15 out of contact with upper limit switch 68″. Contact 34 can then re-open because a current path has been established through contact 68, which closes with switch 68″ becoming unactuated together with contact 83 while contact 68′ opens. The notation adopted in FIG. 3 for labeling switch contacts is that of using corresponding numbers to identify each contact of a pair provided in a double throw switch, numbers with a prime superscript being normally open when the associated switch is not actuated. Upon continuing descent of follower 15 down shaft 14, electrode 59 is brought into contact with water within instrument 10, thereby to complete a circuit through sensing relay 40 which closes contacts 41′ and 42′, with a current path being provided through the former contact to reversing relay holding coil 35. The enernization of coil 35 actuates a three pole double throw switch relay comprising contacts, 36, 36′, 37, 37′, 38, 38′ and a two pole single throw switch relay comprising contacts 39′ and 79′. With the cross switching occurring between contacts 36, 36′ and 37, 37′ when coil 35 is energized, motor 13 reverses rotation and follower 15 is traversed upwardly on shaft 14 removing electrode 59 from contact with water, and engaging retaining clip 61 to lift valve rod 49 opening water valve 54, and finally tripping limit switch 68″ to close contact 68′ and open contacts 68 and 83, stopping motor 13. Current flow continues through coil 35 maintaining contacts 36′, 37′, 38′, 39′ and 79′ in open position. Water rising in instrument 10 immerses electrode 60 to again energize sensing relay coil 40 and close contacts 41 and 42, the latter providing a current path to coil 67 of solenoid operator 67″. Ratchet arm 65 is operably biased by actuation of solenoid operator 67″ to dislodge retaining clip 61 from support on follower 15, dropping valve rod 49 and causing valve 54 to close, and to open contacts 81 and 82 interrupting the circuits to both coils 35 and 67. With all circuits open except through contact 38 to clock timed switch 17, all contacts return to the normally open or normally closed state of non-actuation, and current is drawn from battery 12 only by clock timed switch 17 during the time interval until commencement of the next operational cycle of the instrument.

One embodiment of the instrument of this invention has been described with particularly, but variations and alternatives of the described embodiment will suggest themselves to persons skilled in the art, however, the essential requirement of this invention is the provision of a vertically traversing electrode driven by a reversibly operable motor to sense water level differential at timed inervals.

We claim:

1. A liquid level controller comprising in combination:

a. a reversibly drivable electric motor,
b. an output shaft for said electric motor,
c. an electrode mounted to be traversed longitudinally of said output shaft by operation of said electric motor rotating said shaft,
d. a reversing switch for said electric motor wherein said reversing switch is actuated by said elctrode coming into contact with a body of electrically conductive liquid to establish an electric current path therethrough,
e. a supply valve for electrically conductive liquid,
f. valve biasing means for said supply valve actuated by traverse of said electrode,
g. a timer controlled switch for energizing said electric motor,
h. a motor de-energizing switch actuated by traverse of said electrode, said controller functioning in repetitive cycles wherein said conductive liquid may issue from said supply valve to fill a confined space, which is traversed by said electrode driven by said timer controlled switch operated motor for periodically sensing liquid elevation in the confined space, a motor reversing circuit being completed by said electrode making contact with conducting liquid to actuate retrival of said probe and replenishment of liquid to datum level in the confined space.

2. The apparatus of claim 1 comprising a reservoir for containing a supply of said electrically conductive liquid.

3. The apparatus of claim 1 wherein said output shaft comprises screw lead threading for operable traversing of said electrode.

4. The apparatus of claim 1 comprising a stylus carried by said electrode and a sheet of paper for being marked by said stylus.

5. The apparatus of claim 1 comprising a self-contained power source.

6. The apparatus of claim 1 wherein said liquid level controller is of elongated configuration for operable insertion into a bore hole for use as a soil percolation testing instrument.

* * * * *